(12) United States Patent
Ekwall et al.

(10) Patent No.: US 6,233,486 B1
(45) Date of Patent: May 15, 2001

(54) ISCHEMIA DETECTOR AND HEART STIMULATOR PROVIDED WITH SUCH AN ISCHEMIA DETECTOR

(75) Inventors: Christer Ekwall; Christina Nyhlén, both of Spånga (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/341,944

(22) PCT Filed: Jan. 13, 1998

(86) PCT No.: PCT/SE98/00042

§ 371 Date: Jul. 20, 1999

§ 102(e) Date: Jul. 20, 1999

(87) PCT Pub. No.: WO98/31279

PCT Pub. Date: Jul. 23, 1998

(30) Foreign Application Priority Data

Jan. 22, 1997 (SE) .................................................... 9700181

(51) Int. Cl.[7] .................................................... A61B 5/00
(52) U.S. Cl. ................. 607/17; 607/18; 607/23; 600/481; 600/485
(58) Field of Search ...................... 607/17, 23; 600/481, 600/485

(56) References Cited

U.S. PATENT DOCUMENTS

| 4,791,931 | | 12/1988 | Slate . | |
|---|---|---|---|---|
| 4,821,735 | | 4/1989 | Goor et al. . | |
| 5,025,786 | | 6/1991 | Siegel . | |
| 5,330,505 | * | 7/1994 | Cohen | 607/6 |
| 5,427,112 | | 6/1995 | Noren et al. . | |
| 5,476,484 | * | 12/1995 | Hedberg | 607/23 |
| 5,497,780 | | 3/1996 | Zehender . | |
| 5,700,283 | * | 12/1997 | Salo | 607/23 |
| 6,021,350 | * | 2/2000 | Mathson | 607/17 |

FOREIGN PATENT DOCUMENTS

| 0 178 528 | 4/1986 | (EP) . |
|---|---|---|
| 0 721 786 | 7/1996 | (EP) . |

* cited by examiner

Primary Examiner—Robert L. Nasser
(74) Attorney, Agent, or Firm—Schiff Hardin & Waite

(57) ABSTRACT

An ischemia detector has a sensor unit which determines the systolic pressure of a subject, a unit wherein a relation is established between the systolic pressure and the subject's heart rate, as the heart rate is varied over a range, and an analyzer which determines the occurrence of ischemia from this relation.

23 Claims, 4 Drawing Sheets

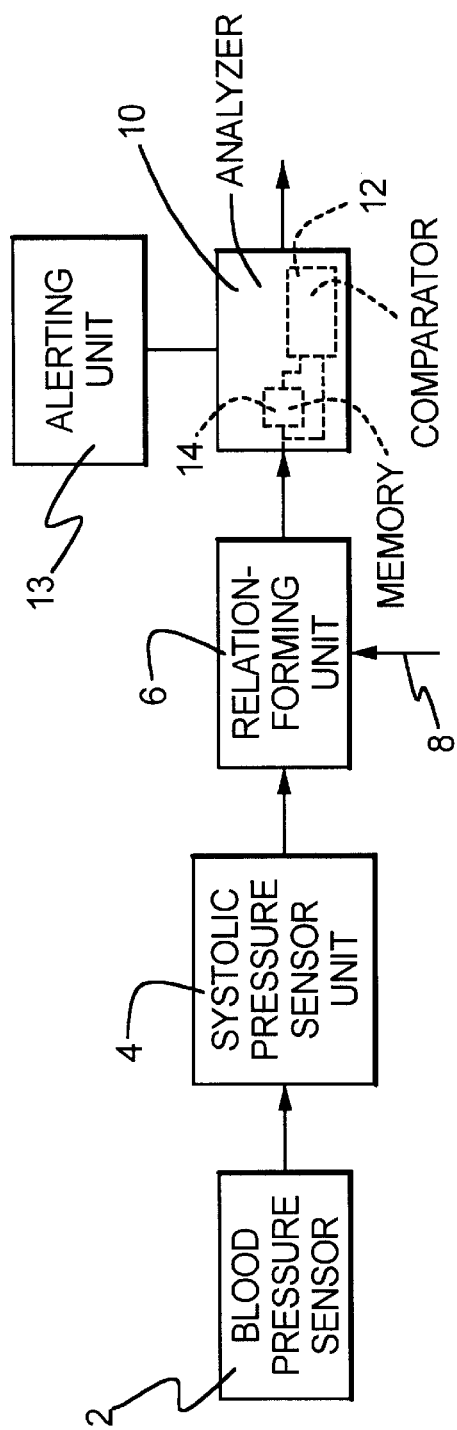
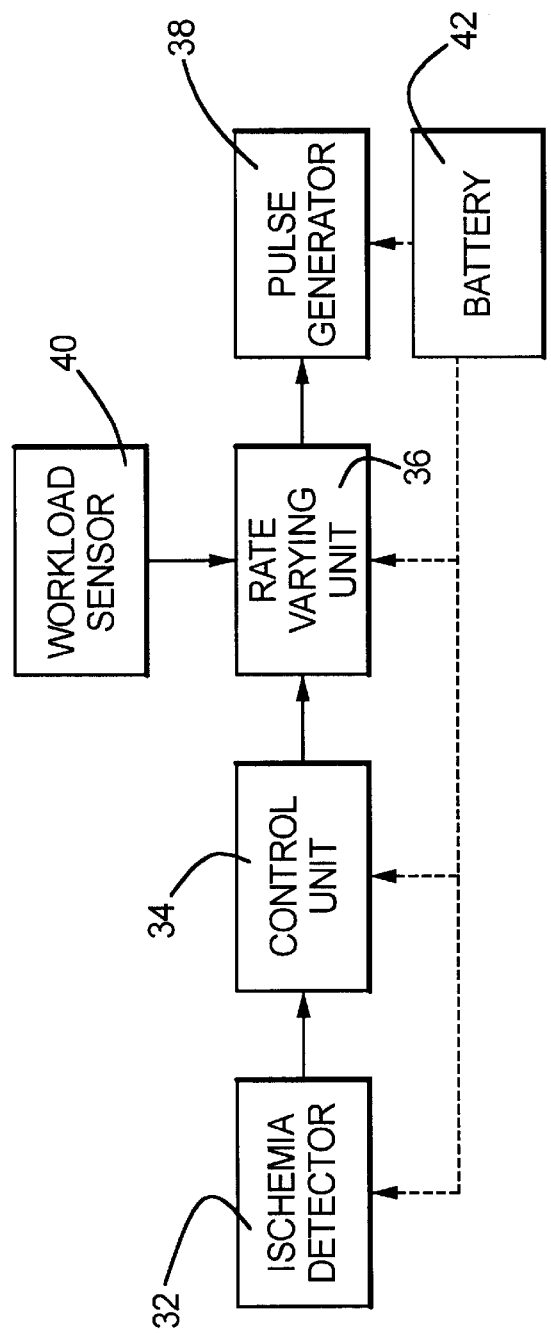
FIG. 3
FIG. 7

ISCHEMIA DETECTOR AND HEART STIMULATOR PROVIDED WITH SUCH AN ISCHEMIA DETECTOR

TECHNICAL FIELD

The present invention relates to an ischemia detector and to a heart stimulator having such an ischemia detector.

BACKGROUND ART

The blood flow and penetration in the circulatory system of a living subject is dependent on the arteriole muscular tension, so-called tonus. A high tonus reduces the arteriole diameter and as a result the blood flow is reduced. The driving force of the flow is the aortic blood pressure. The elasticity of the aorta maintains the blood flow between heart contractions. Variations in the aortic pressure have a limited, secondary effect on the blood flow.

The tension of the arteriole muscles is released by an epidermal releasing factor (EDRF), in practice NO-gas, which is emitted by the arteriole inner epidermal tissue. The emission of EDRF is inhibited by hemoglobin. The arteriole muscular tension is asserted by neural system controlled demand. For local control this tension is released by EDRF and the release of EDRF is in its turn inhibited by the blood flow, as mentioned above. By the combined action of EDRF and the blood flow the blood distribution to different parts of the body of a living subject is controlled and it is possible to compensate for local pressure differences, lumen diameters etc.

With the tonus unchanged, an increased heart rate will not result in a significant increase of the blood flow. On the other hand, a decrease in tonus will increase the blood flow, and then the aortic pressure will fall, if the heart rate does not increase at the same time. An increased heart rate is normally controlled by the sinus node and catecholamine hormones. The sinus node controls the over all rate and the catecholamine hormones the propagation speed and contractibility of the heart muscle cells. The onset of both the sinus node control and the catecholamine hormones control is controlled by the autonomous nerve system.

In summary, the blood flow is controlled by the tonus, the driving force for the flow is the blood pressure in the elastic aorta, and the pressure in the aorta is maintained by the pumping action of the heart. During the pumping, the pressure in the left ventricle of the heart is equal to the aortic pressure as long as the aortic valve is open, the systolic phase. The right and left ventricles are parts of two systems, connected in series via the pulmonary system. From each ventricle the same volume of blood is pumped, however, at different pressures. The pressure in the left ventricle is approximately seven times higher than in the right ventricle. The same muscle is producing the pumping force, but the wall of the left ventricle is thicker than the wall of the right ventricle, see FIG. 1, which illustrates the pressures in the left ventricle $P_{LV}$ and in the right ventricle $P_{RV}$ as well as the aortic pressure $P_{aorta}$ as a function of time.

After closing the aortic valve the aortic pressure is exponentially decaying, the decay time being related to the peripheral resistance of the circulatory system or tonus. For a higher workload the blood flow increases and the aortic pressure $P_{aorta}$ decays more rapidly, see FIG. 2, which is a diagram analogous to that in FIG. 1.

If the delivery of stimulation pulses is triggered by a given minimum aortic pressure level the stimulation rate will be increased in response in response to an increased workload, so-called rate response stimulation. If the stimulus is moved to an earlier timing position, the systolic pressure will start from a higher starting pressure and hence a higher end systolic pressure should result. However, this is not the case if the heart is ischemic. The pumping of the heart is then less effective and the blood volume output per heartbeat is less and no pressure increase will result.

For the pumping action the heart needs energy in the form of oxygen and glucose. About 60% of the oxygen in the heart interstitial fluid is consumed within one heartbeat. If the energy supply to the heart is disturbed the heart contractability and the pumping action of the heart are severely deteriorated and an oxygen shortage or ischemic situation will rapidly develop.

Ischemia results from insufficient blood flow through the heart muscle. The reason therefor is blocking or passage congestion of coronary blood vessels of the heart. There are three categories of ischemic deceases, viz. angina pectoris, heart infarction and heart insufficiency and an ischemia is experienced by the patient as a severe chest pain.

During systole when the aortic valve is open, no blood can flow to the heart muscle. The pressure inside the heart is substantially equal to the aortic blood pressure. After closure of the aortic valve, some time is needed for the oxygen delivery to the heart muscle such that contractability is regained. In case of coronary blood vessel congestion this time is considerably increased. It is known that the developement of an ischemia accelerates with increasing heart rate, i.e. increasing workload. In a pacemaker system with a stimulation rate that increases with increasing workload, ischemia is a major limitation for the rate increase. As blood penetration of the heart muscle is possible only during diastole, when the aortic pressure is higher than the ventricular pressure, a rate increase, which results in a reduction of the diastolic period, will severe the ischemic situation, cf. FIG. 2. As mentioned above, in a deceased heart the normal rate control by the sinus node is lost. A pacemaker is therefore needed to maintain a proper heart rate and different systems are used to adjust the stimulation rate to increased demands, associated with e.g. increased workload. The ischemic effect can be especially serious for patients having such rate response pacemakers.

A method and apparatus for detecting myocardial ischemia is described in U.S. Pat. No. 4,821,735. The systemic vascular resistance (SVR) in a subject is then monitored and the presence of myocardial ischemia is detected when the SVR increases by at least 60% over a base line value, said SVR being defined as the ratio between the arterial pressure P and the peak dP/dt at the time of the peak of the dP/dt.

A device for analyzing the function of a heart is described in U.S. Pat. No. 5,427,112. A heart variable is then measured and a parameter signal related to the heart variable is generated, whereupon the heart variable is plotted against the parameter signal to obtain a curve. By analyzing the morphology and chronological course of the curve functional aberrations of the heart, such as bradycardia, tachyarrhythmia, ischemia etc., can be detected.

In U.S. Pat. No. 5,497,780 an apparatus is described for determining an ischemia by measurements of electric potentials between at least three implanted measuring electrodes, two of said electrodes being implanted with their poles in the heart and the third electrode being implanted with its pole lying outside the heart.

In U.S. Pat. No. 5,476,484 an apparatus is disclosed for determining the peripheral resistance to flow in a living subject by measuring changes in the pressure drop in an artery during diastole for determining the physical condition of the subject, like state of health or workload (activity level). A rate-responsive heart stimulator is then controlled dependent on this peripheral resistance.

The purpose of the present invention is to provide a new reliable ischemia detector, which can be used also for eliminating the above discussed problems for ischemic patients carrying a heart stimulator.

DISCLOSURE OF THE INVENTION

The above object is achieved in accordance with the principles of the present invention in an ischemia detector, and a heart stimulator, having a sensor unit which determines systolic pressure in a subject, means for establishing a relation between the systolic pressure and the heart rate of the subject as the heart rate of the subject varies, and analyzer means for determining the occurrence of ischemia from this relation. In a non-symptomatic, normal heart there exists a relation between the systolic pressure and the length of the time interval between successive heart contractions For longer intervals between the contractions a lower aortic, systolic pressure results. For shorter intervals the pressure increases. For very short intervals between successive heart beats other factors, such as heart supply and venous blood return, may be of importance. In the detector according to the invention the length of the intervals or the heart rate is thus varied around a normal heart rate and the corresponding systolic pressure is measured. In this way a relation between heart rate and systolic pressure is established and by analyzing this relation, i.e. by analyzing the shape of the corresponding curve, e.g. its slope and/or bending, the occurrence of an ischemia can be determined. This measured relation can also be used for controlling a pacemaker to prevent its stimulation rate not to exceed a maximum ischemic prevention rate, this maximum rate being the maximum rate for which the systolic pressure increases or at least stays at the same level. Alternatively, instead of studying the systolic pressure as a function of the heart rate, an ischemia can be detected from the relation between the difference between the end systolic pressure and the end diastolic pressure as a function of the heart rate. As the end diastolic pressure is low and close to the atmospheric pressure the two techniques will give practically the same result.

According to an advantageous embodiment of the detector according to the invention the analyzer means are arranged to determine a decreasing systolic pressure with increasing heart rate as an indication of an ischemia, and according to another embodiment of the detector according to the invention a still more reliable indication of an ischemia is obtained by arranging the analyzer means to determine a decreasing systolic pressure with increasing heart rate followed by an increasing systolic pressure with decreasing heart rate as an indication of an ischemia.

According to yet another advantageous embodiment of the detector according to the invention the analyzer means comprise a comparator for comparing the systolic pressure from one heartbeat to the systolic pressure from the next one. In this way a practical realization of the detector according to the invention is possible.

According to still other advantageous embodiments of the detector according to the invention the sensor unit is provided to measure the systolic pressure in the right ventricle. This pressure differs from the systolic aortic pressure by just a multiplication factor and the benefits of implementing the sensor unit in the right ventricle include easier implementation, reduced risk for thrombosis and the sensor unit can be combined with a stimulating and possible rate response sensing electrode. In the case where the detector is used with a heart stimulator the sensor can preferably be mounted behind the stimulation tip on a heart stimulator lead.

According to one advantageous embodiment more of the detector according to the invention the analyzer means are arranged to disable the rate response function as soon as increased stimulation rate does not result in an increased systolic pressure, in the case where the heart stimulator is a rate response pacemaker. This is of great importance, since a rate response function resulting in an increased heart rate in response to an increased workload tends to accelerate the developement of the ischemia and thus to severe the ischemic situation of the patient.

According to yet other advantageous embodiments of detector according to the invention alerting means are disposed to be activated in response to a detected ischemia, said alerting means preferably being arranged to be activated by said analyzer means in response to a determined occurence of an ischemia for alerting the patient. This is of particular value to patients having silent ischemias, the occurence of which the patient otherwise would not be aware of. When being alerted it is also possible for the patient himself or herself to temporarily lower his or her activity.

Consequently, according to another aspect of the invention, a heart stimulator is proposed having means for varying the stimulation rate and an ischemia detector as defined above.

According to advantageous embodiments of the invention in this aspect, the heart stimulator comprises control means connected to the ischemia detector for controlling the stimulation rate varying of an ischemia, preferably to a maximum allowable rate for which the developement of an ischemia is avoided or to a baserate.

BRIEF DESCRIPTION OF THE DRAWINGS

To explain the invention more in detail as examples chosen embodiments of the invention are described more in detail with reference to the drawings, on which FIG. 3 is a block diagram of an embodiment of an ischemia detector according to the invention, FIG. 7 shows a block diagram of the essential parts of a rate response heart stimulator equipped with an ischemia detector.

DESCRIPTION OF PREFERRED EMBODIMENTS

Figure 1:
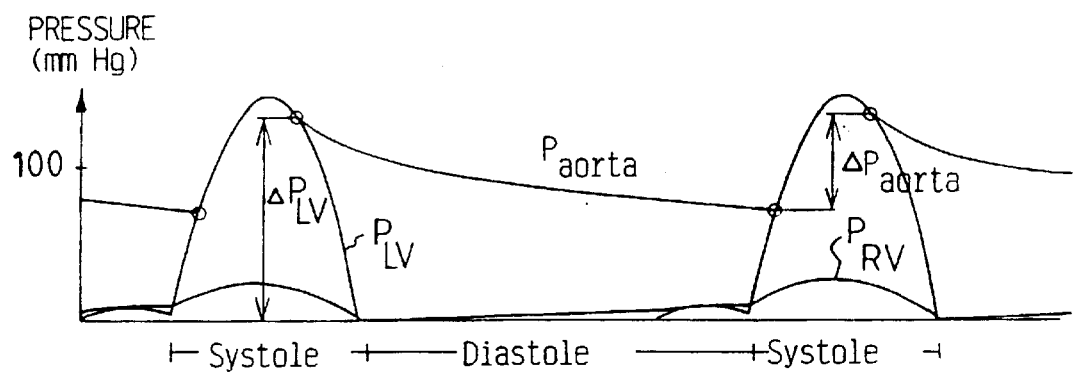
FIGS. 1 and 2 show the pressures in the left and right ventricles as well as the aortic pressure as a function of time for two different heart rates.
Figure 2:
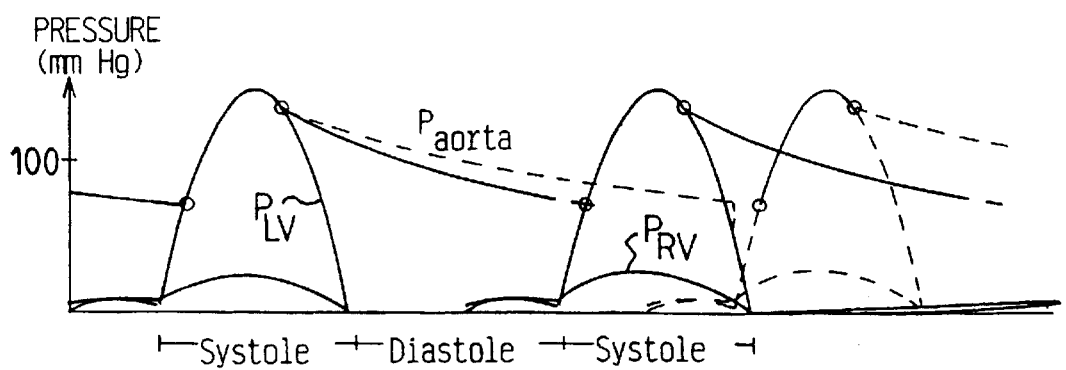

FIGS. 1 and 2 show the pressures in the left ventricle $P_{LV}$ and in the right ventricle $P_{RV}$ as well as the aortic pressure $P_{aorta}$ as a function of time for two different heart rates.

During systole the pressure in the left ventricle is equal to the pressure in the aorta and no cardiac blood flow and oxygen supply to heart tissue takes place. During diastole the aortic pressure decays depending on the peripheral resistance of the circulatory system. $-P_{LV}$ and $-P_{aorta}$ denote the increases if the pressures in the left ventricle and in the aorta respectively during a heartbeat. FIG. 2 illustrates the pressures in the ventricles and the aorta for a heart rate increased vis-a-vis the rate in FIG. 1 due to an increased workload. However, this is not the result if the heart is ischemic. The pumping action of the heart is then less effective and no increase of the end systolic pressure will result. From FIGS. 1 and 2 it also appears that an increased heart rate results in a shortened diastolic phase, during which oxygen exchange to the heart takes place. Thus an increased heart rate due to an increased workload or an increased stimulation rate will normally worsen an ischemic state of the heart.

FIG. 3 shows the block diagram of an embodiment of the ischemia detector according to the invention. The detector comprises a sensor 2 for measuring the blood pressure, connected to a sensor unit 4 for determining the systolic pressure. Means 6 are further provided for establishing a relation between systolic pressure and stimulation rate from a heart stimulator in which the detector is mounted, received over the input 8. This relation is established by measuring the pressure as a function of the stimulation rate when varying the stimulation rate. Analyzer means 10 are further connected to the establishing means 6 for determining the occurence of an ischemia by analyzing the relation between systolic,pressure and stimulation rate. For this purpose the analyzer includes 10 a comparator 12 for comparing the systolic pressure from one heart beat to the systolic pressure from the next heart beat. A memory 14 is then also provided in the analyzer 10 for storing the measured pressure during one heart beat for the comparison with the pressure of the next heart beat.

The detector is also provided with alerting means 13, e.g. of a wristwatches "beeper-type". These alerting unit 13 are connected to the analyzer means 10 to be activated by a detected ischemia, The alerting 13 are of particular value for patients having a "silent ischemia", the occurrence of which the patient otherwise would not be aware of.

Figure 4:
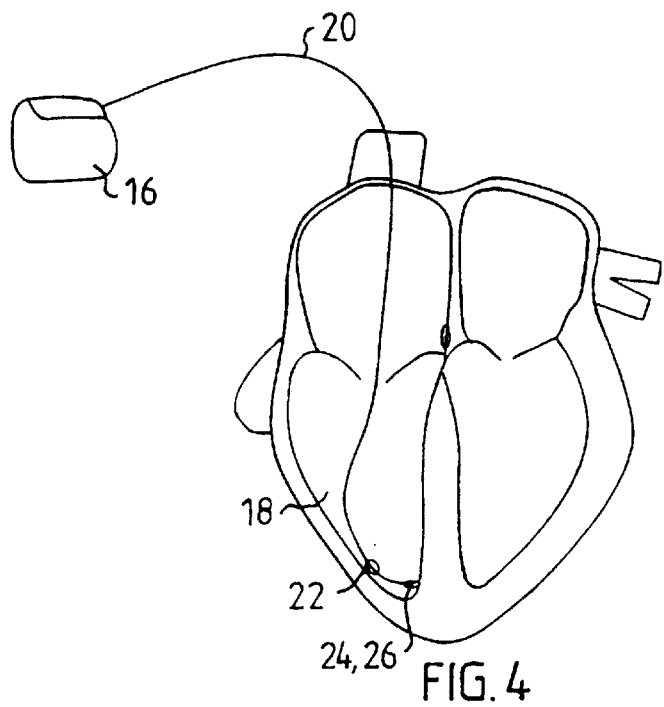
FIG. 4 shows a pacemaker with its electrode lead implanted in the right ventricle, said lead having electrodes and a pressure sensor for an ischemia detector according to the invention.

FIG. 4 shows an implanted pacemaker 16, connected to heart tissue of the wall of the right ventricle 18, by its electrode lead 20. The lead 20 is of bipolar type with an electrode ring 22 and with a tip electrode 24 and a pressure sensor 26 provided at the distal end portion of the lead 20, cf. FIG. 5. With this type of lead 20 it is possible to stimulate the heart, sense electrical activity in the wall tissue and sense contraction pressure of both spontaneous and stimulated heart beats.

As mentioned above the systolic aortic pressure is the relevant parameter for the ischemia detection according to the invention, however, the systolic pressure in the right ventricle reflects the aortic pressure and there are benefits of measuring in the right ventricle. As a matter of fact the systolic aortic pressure and the systolic pressure in the right ventricle differs only by a multiplication factor of approximately seven.

Figure 6:
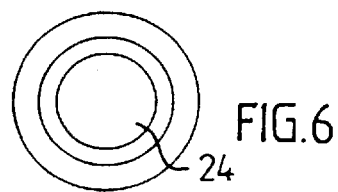
FIGS. 5 and 6 show on an enlarged scale the distal end portion of the lead in FIG. 4.
Figure 5:
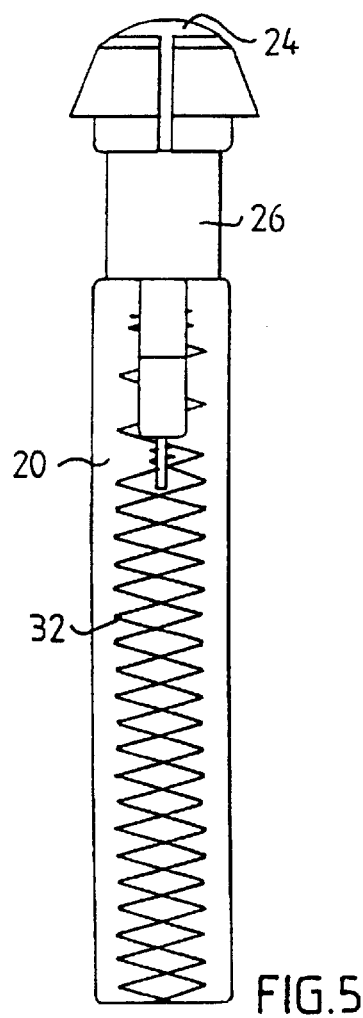

FIGS. 5 and 6 show the distal end portion of the electrode lead in FIG. 4 on an enlarged scale in longitudinal cross section and in end view respectively. The sensor 26 is placed just behind the tip electrode 24 for stimulation of the heart. The sensor 26 comprises a stiff cylindrical device of a piezoelectric material. Cloture and overgrowth will not affect the sensing properties of the sensor 26. A helical conductor 32 inside the lead 20 connects the electrode 24 to the electronics in the pacemaker 16.

FIG. 7 shows a block diagram of a heart stimulator with an ischemia detector 32 of the type described above. The detector 32 is connected to control means 34, which are disposed to control stimulation rate varying 36. The heart stimulator is a rate response pacemaker and a workload sensor 40 is connected to the stimulation rate varying means 36 to adapt the rate of the stimulation pulse generator 38 to the workload of the living subject. A battery 42 is provided as source of electric energy of the heart stimulator.

It is also possible to use the pressure sensor 26 of the ischemic detector 32 as workload sensor.

When an ischemia is detected by the detector 32 the control means 34 control the stimulation rate varying means 36 to lower the rate of stimulation pulses delivered by the pulse generator 38. The pulse rate is preferably lowered to the maximum allowable stimulation rate for which the developement of an ischemia still is avoided. Alternatively, the stimulation rate is lowered to a baserate, below a stimulation rate which can give rise to an ischemia.

Figure 8:
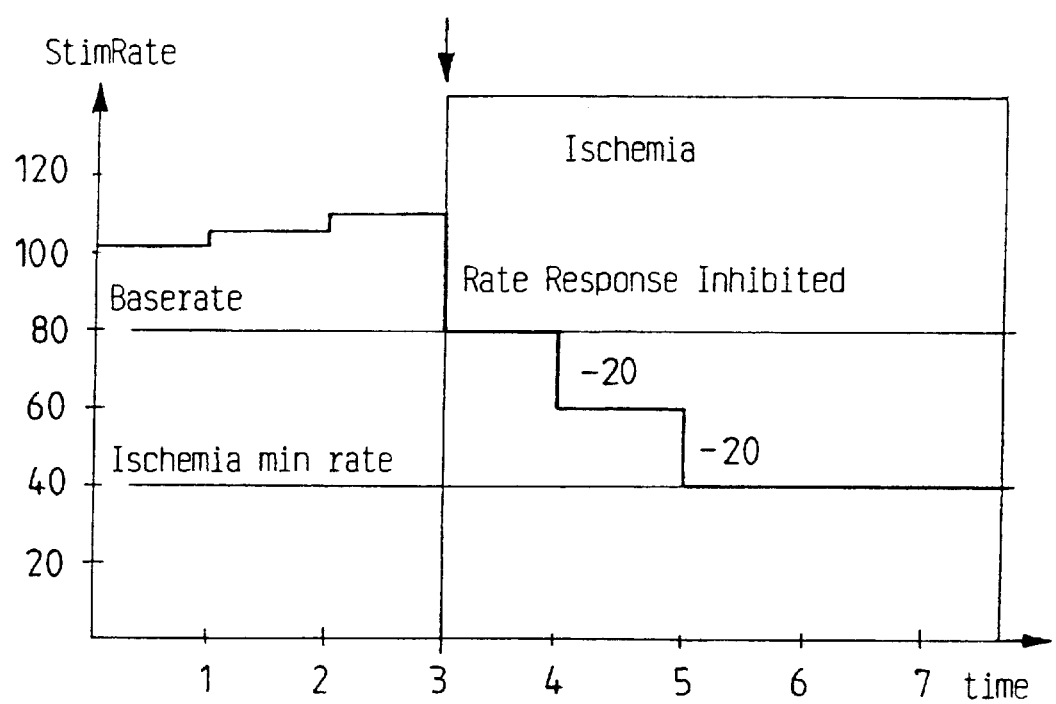
FIG. 8 shows a diagram for illustrating the function of the stimulator shown in FIG. 7.

The regulation of the stimulation rate of the heart stimulator when an ischemia is detected is illustrated in FIG. 8, which shows the stimulation rate in pulses per minute versus time in an arbitrary scale. Thus in the time interval 1–3 the heart stimulator is in a rate response mode of operation. At time 3 an ischemia is detected and the rate response function of the heart stimulator is inhibited and the stimulation rate is lowered to a baserate. At time 4 the stimulation rate is further lowered with pulses per minute to try to cure the ischemic state of the patient and at time 5 the stimulation rate is lowered with another 20 pulses per minute if the ischemic state persists, an ischemia minimum rate then being reached.

In the above described embodiments of the ischemia detector according to the invention the systolic pressure related to the atmospheric pressure is used as a relevant parameter. As an alternative the ischemia detector according to the invention can be based on the pressure increase obtained during a heartbeat, i.e. the difference between the end systolic pressure and the end diastolic pressure, the end systolic pressure being the highest pressure after a completed heart contraction and end diastolic pressure being the lowest pressure just before the next heart contraction, cf. FIGS. 1 and 2.

As discussed above an ischemia reduces the pumping efficiency of the heart, which results in a reduced ability to increase the pressure during a heart beat. As a result of a reduced pumping efficiency due to an ischemia there will also be a larger quantity of the total blood volume on the venous side of the circulatory system than in a normal situation, which means that the heart is operating with a lower pressure difference where both the lower level is raised and the upper level is lowered. Thus from a theoretical point of view the above mentioned difference between the end systolic and the end diastolic pressures should be the most relevant quantity to base the detector according to the invention on. However, in most cases the diastolic pressure is low and near the atmospheric pressure and therefore the two alternatives of ischemia detector will in practice function equally well.

The embodiment of the ischemia detector according to the invention shown in FIG. 1 can be easily modified to be based on measurement of the difference between the end systolic and the diastolic pressures. The sensor 2 and the sensing unit 4 are then disposed to determine this pressure difference and the means 6 are arranged to determine a relation between the pressure difference: and the stimulation rate.

Although modifications and changes may be suggested by those skilled in the art, it is the intention of the inventors to embody within the patent warranted hereon all changes and modifications as reasonably and properly come within the scope of their contribution to the art.

What is claimed is:

1. An ischemia detector, comprising a sensor unit which emits a signal representing systolic pressure of a subject, means for establishing a relation between said systolic pressure and a heart rate of a subject over a plurality of varying heart rates, and analyzer means for determining an occurrence of ischemia from said relation.

2. The detector according to claim 1, wherein said analyzer means identifies a decreasing systolic pressure with increasing heart rate as an occurrence of ischemia.

3. The detector according to claim 2 wherein said analyzer means comprise comparator means for comparing the systolic pressure from one heartbeat to the systolic pressure from a next heartbeat to determine whether a relationship of heartbeat-to-heartbeat systolic pressures exists that is indicative of ischemia.

4. The detector according to claim 1 wherein said analyzer means identifies a decreasing systolic pressure with increasing heart rate followed by an increasing systolic pressure with decreasing heart rate as an occurrence of ischemia.

5. The detector according to claim 4, wherein said analyzer means comprise comparator means for comparing the systolic pressure from one heartbeat to the systolic pressure from a next heartbeat to determine whether a relationship of heartbeat-to-heartbeat systolic pressures exists that is indicative of ischemia.

6. The detector according to claim 1 wherein said sensor unit measures the systolic pressure in the right ventricle of a subject.

7. The detector according to claim 1 further comprising an alerting unit which is activated in response to a detected occurrence of ischemia.

8. The detector according to claim 7, wherein said alerting device is activated by said analyzer means in response to a detected occurrence of ischemia.

9. An ischemia detector comprising a sensor unit which determines a pressure difference between an end systolic pressure and an end diastolic pressure of a subject, means for establishing a relation between said pressure difference a heart rate of a subject when over a plurality of heart rates, and analyzer means for determining an occurrence of ischemia from said relation.

10. The detector according to claim 9 further comprising an alerting unit which is activated in response to a detected occurrence of ischemia.

11. The detector according to claim 10 wherein said alerting unit is activated by said analyzer means in response to a detected occurrence of ischemia.

12. A heart stimulator comprising:

a pulse generator which emits stimulation pulses at a stimulation rate;

an electrode lead connected to said pulse generator and adapted for in vivo implantation in a subject to deliver said stimulation pulses to cardiac tissue, said electrode lead having at least one electrode adapted for contact with cardiac tissue;

means for operating said stimulation generator to vary said pulse rate over a plurality of stimulation rates; and an ischemia detector comprising a sensor unit which emits a signal representing systolic pressure of a subject receiving said stimulation pulses, means for establishing a relation between said systolic pressure and a heart rate of a subject over a plurality of heart rates represented by said plurality of stimulation rates, and analyzer means for determining an occurrence of ischemia from said relation.

13. The heart stimulator according to claim 12 wherein said at least one electrode comprises a tip electrode and wherein said sensor unit comprises a sensor mounted behind the electrode tip on said electrode lead.

14. The heart stimulator according to claim 12 further comprising a control unit for controlling said pulse generator in a rate responsive mode and wherein said analyzer means is connected to said control unit to disable the rate responsive mode as soon as an increased stimulation rate does not result in an increased systolic pressure.

15. The heart stimulator according to claim 12 further comprising control means connected to the ischemia detector for controlling the stimulation rate varying means to lower the stimulation rate in response to a detection of an occurrence of ischemia.

16. The heart stimulator according to claim 15, wherein said control means control said stimulation rate varying means to lower the stimulation rate to a maximum stimulation rate for which an occurrence of ischemia is not detected.

17. The heart stimulator according to claim 15, wherein said control means control said stimulation rate varying means to lower the stimulation rate to a base rate, below a stimulation rate at which an occurrence of ischemia is detected.

18. A heart stimulator comprising:

a pulse generator which emits stimulation pulses at a stimulation rate;

an electrode lead connected to said pulse generator and adapted for in vivo implantation in a subject to deliver said stimulation pulses to cardiac tissue, said electrode lead having at least one electrode adapted for contact with cardiac tissue;

means for operating said stimulation generator to vary said pulse rate over a plurality of stimulation rates; and an ischemia detector comprising a sensor unit which determines a pressure difference between an end systolic pressure and an end diastolic pressure of a subject, means for establishing a relation between said pressure difference and a heart rate of a subject over a plurality of heart rates represented by said plurality of rates rates, and analyzer means for determining an occurrence of ischemia from said relation.

19. The heart stimulator according to claim 18 wherein said at least one electrode is a tip electrode and wherein said sensor unit comprises a sensor mounted behind the tip electrode on said electrode lead.

20. The heart stimulator according to claim 18 further comprising a control unit for controlling said pulse generator in a rate responsive mode and wherein said analyzer means is connected to said control unit to disable the rate responsive mode as soon as an increased stimulation rate does not result in an increased systolic pressure.

21. The heart stimulator according to claim 18 further comprising control means connected to the ischemia detector for controlling the stimulation rate varying means to lower the stimulation rate in response to a detection of an occurrence of ischemia.

22. The heart stimulator according to claim 21, wherein said control means control said stimulation rate varying means to lower the stimulation rate to a maximum stimulation rate for which an occurrence of ischemia is not detected.

23. The heart stimulator according to claim 21, wherein said control means control said stimulation rate varying means to lower the stimulation rate to a base rate, below a stimulation rate at which an occurrence of ischemia is detected.

* * * * *